14-09
2/3/85 03 RE 32,303

United States Patent [19]
Lasker et al.

[11] E Patent Number: Re. 32,303
[45] Reissued Date of Patent: Dec. 9, 1986

[54] PERITONEAL DIALYSIS APPARATUS

[75] Inventors: Norman Lasker, Philadelphia, Pa.; Bruce E. Jarrell, Richmond, Va.

[73] Assignee: American Medical Products Corp., Freehold, N.J.

[21] Appl. No.: 781,031

[22] Filed: Mar. 24, 1977

Related U.S. Patent Documents

Reissue of:
[64] Patent No.: 3,872,863
Issued: Mar. 25, 1975
Appl. No.: 384,316
Filed: Jul. 31, 1973

[51] Int. Cl.[4] ..... A61M 5/00; A61M 1/03
[52] U.S. Cl. ..... 604/29
[58] Field of Search ..... 128/213, 214 R, 214 E, 128/214 Z, 227, 230, 273, 274

[56] References Cited

U.S. PATENT DOCUMENTS

| | | | |
|---|---|---|---|
| 2,625,932 | 1/1953 | Salisbury | 128/214.2 |
| 2,707,955 | 5/1955 | Borden | 128/278 |
| 3,410,268 | 11/1968 | Leucci | 128/227 |
| 3,575,161 | 4/1971 | London | 128/214 R X |
| 3,620,215 | 11/1971 | Tysk et al. | 128/213 |
| 3,709,222 | 1/1973 | De Vries | 128/213 |
| 3,730,183 | 5/1973 | Goldsmith et al. | 128/213 |
| 3,783,866 | 1/1974 | Tirkkonen | 128/213 |

FOREIGN PATENT DOCUMENTS

| | | | |
|---|---|---|---|
| 1964588 | 7/1971 | Fed. Rep. of Germany | 128/213 A |
| 1964733 | 7/1971 | Fed. Rep. of Germany | 128/213 A |
| 2017408 | 10/1971 | Fed. Rep. of Germany | 128/213 A |

OTHER PUBLICATIONS

Lasker et al.-Trans. Amer. Soc. Artific. Inter. Orgs., vol. XII, 1966, pp. 94–97.

*Primary Examiner*—Dalton L. Truluck
*Attorney, Agent, or Firm*—Panitch, Schwarze, Jacobs & Nadel

[57] ABSTRACT

A peritoneal dialysis apparatus comprising a plurality of components including a catheter, a fluid heater, a fluid weighing means and a control device. The components are interconnected by conduits so that fluid can flow from the heater to the peritoneal cavity by way of the catheter, and then from the peritoneal cavity to the weighing means. The weighing means measures the quantity of discharged fluid as a result of the introduction of the dialysis fluid to check that the dialysis fluid is causing fluid to drain from the peritoneal cavity. The flow of fluid between the components of the system is controlled by valves which are selectively opened and closed.

11 Claims, 9 Drawing Figures

FIG. 2
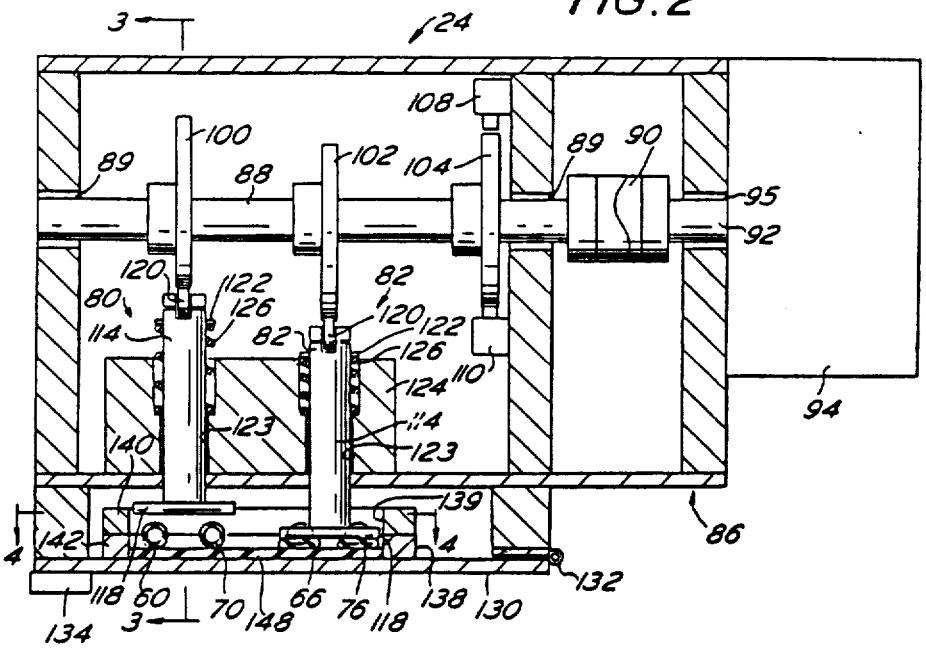
FIG. 4
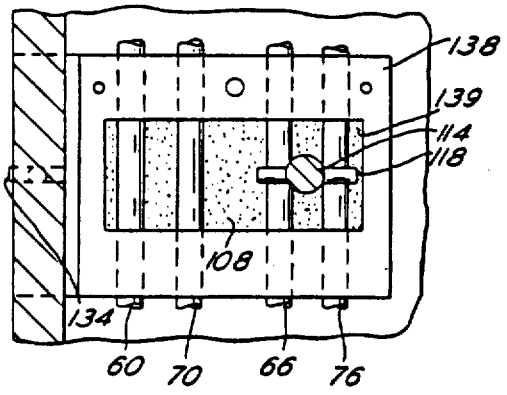
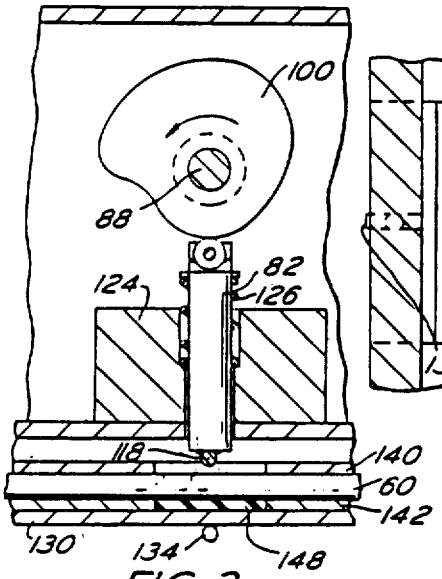
FIG. 3

FIG. 5
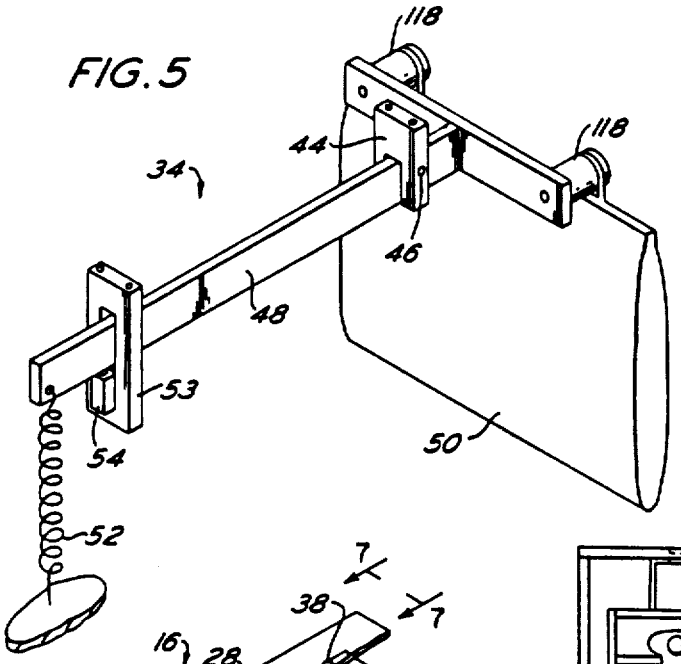
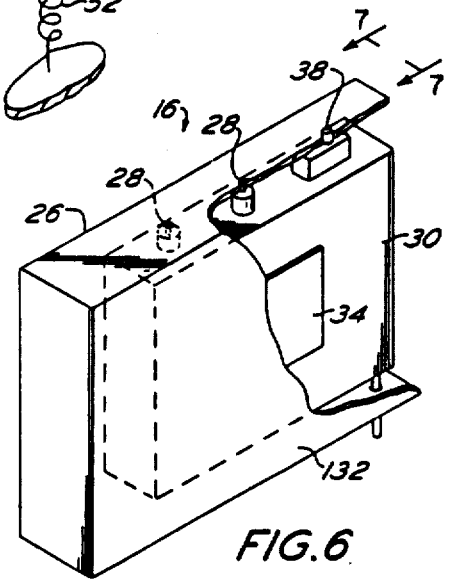
FIG. 6
FIG. 7
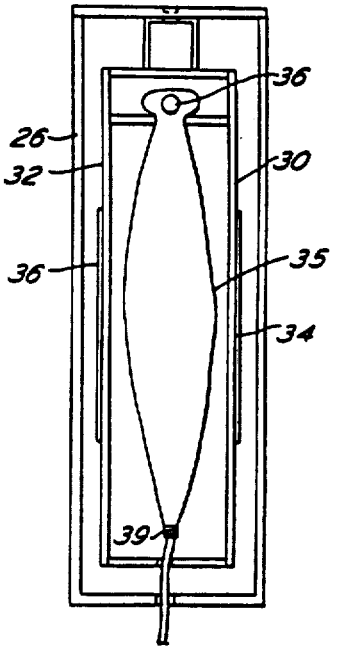

PERITONEAL DIALYSIS APPARATUS

Matter enclosed in heavy brackets [ ] appears in the original patent but forms no part of this reissue specification; matter printed in italics indicates the additions made by reissue.

This invention relates to a dialysis apparatus and more particularly to a peritoneal dialysis apparatus.

Peritoneal dialysis is a well known medical procedure for removing impurities from the blood stream. It is accomplished by introducing a suitable dialysis fluid into the peritoneal cavity and then withdrawing the fluid after a suitable period of time. During the time that the dialysis fluid is in the peritoneal cavity, impurities in the blood stream are drawn through the walls of the blood vessels on the abdominal wall and in the viscera, and through the peritoneum membrane against which they lie through the osmotic effect of the dialysis fluid. The entire procedure may take up to 36 hours since the dialysis fluid must be replaced from time to time as the concentration of impurities in it increase.

Heretofore, peritoneal dialysis has been done in hospitals because of the high risk of infection and because trained personnel need to be available to perform the procedure.

Accordingly, the invention relates to a peritoneal dialysis apparatus which can be used by a patient at home thereby enabling the hospital bed to be free for use by others, and thus reducing the cost of the dialysis to the patient.

To this extent, the apparatus comprises means for supplying dialysis fluid to a means for measuring predetermined quantities and means for conducting the dialysis fluid to a catheter. The catheter is connected to the peritoneal cavity of a patient and to a means for detecting a minimum quantity of dialysis fluid. Means are provided for regulating the flow of dialysis fluid through the apparatus.

The invention can best be described by referring to the attached drawings wherein a presently preferred form of the invention is illustrated and wherein FIG. 1 is a schematic drawing of a preferred form of the apparatus.

FIG. 2 is a sectional view of the means for controlling the flow of fluid through the apparatus.

FIG. 3 is a sectional view taken along line 3—3 of FIG. 2.

FIG. 4 is a sectional view taken along line 4—4 of FIG. 2.

FIG. 5 is a perspective view of a portion of the apparatus illustrated in FIG. 1 for weighing fluid discharged from the peritoneal cavity.

FIG. 6 is a perspective view of a portion of the apparatus shown in FIG. 1 which is used for heating the dialysis liquid.

FIG. 7 is an end view taken along line 7—7 of FIG. 6.

Figure 1:
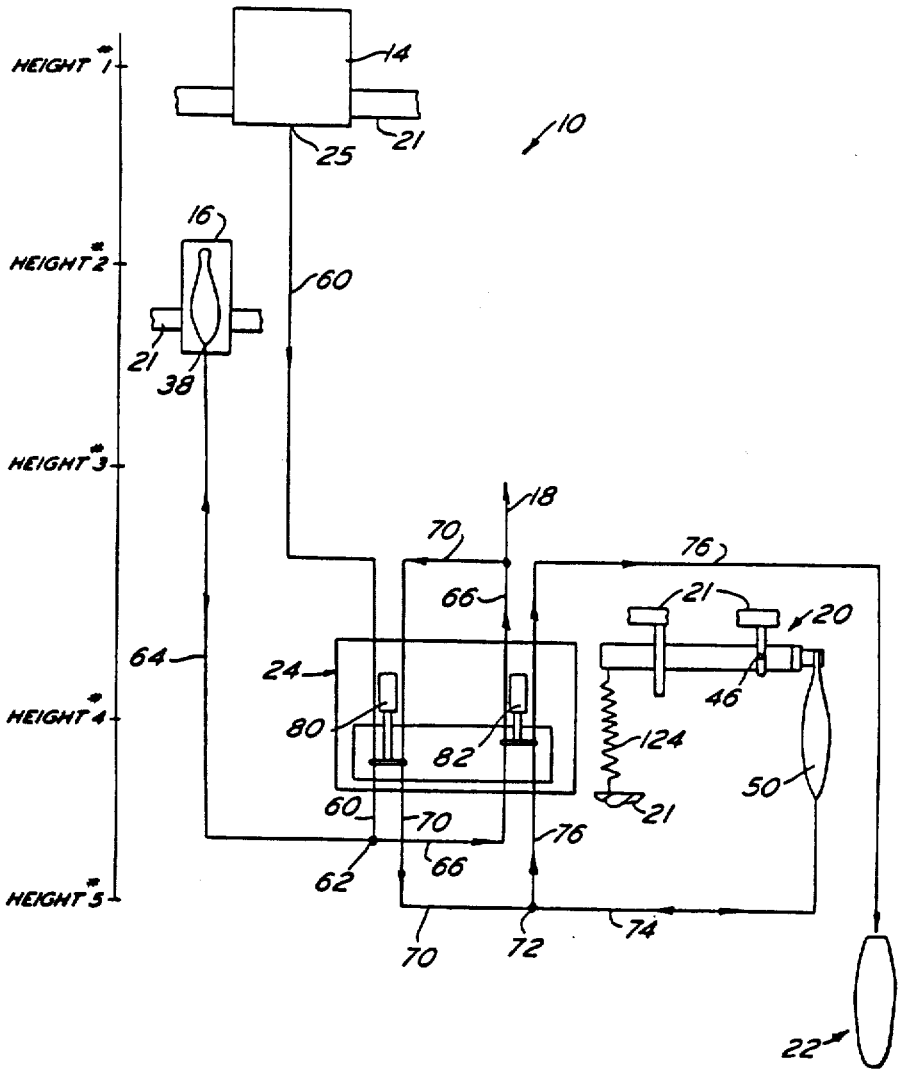

Now referring to the drawing for a detailed description of the invention, a peritoneal dialysis apparatus is schematically illustrated by the numeral 10 in FIG. 1.

The apparatus 10 comprises a container 14 in which a supply of dialysis fluid is stored for use as needed, a means 16 for metering and heating the dialysis fluid after it is dispensed from container 14, a catheter (schematically) 18, a means for detecting discharge of fluid from the patient 20, a means for receiving fluid discharged from the apparatus 22 and a means for controlling the flow of dialysis fluid through the apparatus 24.

A pump or other positive driving means may be used to move the fluid through the apparatus. However, its construction is greatly simplified and its reliability is substantially increased by relying on the force of gravity.

Accordingly, the components of the apparatus are supported by a suitable means indicated schematically by numeral 21 at successively lower heights than the preceding components. The successive components in the apparatus may be interconnected by suitable resilient flexible plastic conduits. A typical plastic is commercially available and is sold as tubing under the trademark "TYGON."

The container 14 may be of any convenient size. Preferably it should contain enough dialysis fluid to enable a complete dialysis procedure to be performed and should be constructed so that the dialysis fluid can be kept sterile. An outlet 25 in the bottom of the container connects it with the rest of the system. Fluid used in peritoneal dialysis are commercially available and are well known to those skilled in the art. A typical fluid is sold under the trademark "DIANEAL" by Travenol Laboratories.

The means for metering and heating the dialysis fluid 16 is best seen in FIGS. 6 and 7. It includes an outer housing 26 which may be of any convenient shape. A heating unit is supported in housing 26 by a plurality of fasteners 28. It comprises front and rear thermally conductive plates 30 and 32 which are arranged in spaced parallel relation to each other. Each of plates 30 and 32 supports a heating element 34 and 36. The heating elements cover a substantial area of plates 30 and 32 to rapidly bring the plates to the desired temperature. A collapsible sterile bag 35 which may be made from "TYGON" is supported within housing 26. A typical means for supporting the bag may include suspending it from a rod 36 which is slipped through a sleeve along one edge of the bag. The bag 35 may have any convenient volume. However it is preferred that the volume be about two liters since introduction and discharge of this volume of fluid into the peritoneal cavity at intervals during the procedure achieves satisfactory results. A bag of reduced volume may be selected when the patient is a child.

The plates 30 and 32 are connected in a circuit which enables them to bring the dialysis fluid in bag 35 to a temperature of about 30° C. The circuit which will be described herein includes a thermal switch 38 in contact with the bag 35. An outlet 39 in the bottom of the bag connects it to the rest of the apparatus. Since the bag 35 is collapsible it can be filled and emptied without exposing its contents to the air.

The catheter 18 may be permanently implanted in the patient or it may be a disposable catheter. Both types of catheters are well known and are commercially available for use in peritoneal dialysis.

The means for detecting discharge of fluid from the patient 20 can best be seen in FIG. 5. It may be mounted to a support frame (not shown) by a bracket 44. The bracket supports a pin 46 which serves as a fulcrum for an elongated lever arm 48. A collapsible bag 50 for collecting fluid discharged from the patient is supported at one end of lever arm 48. The other end of lever arm 48 is connected to a counterweight such as spring 52. A second bracket 53 on the support frame carries a microswitch 54 so that the operator of the microswitch is in contact with the lower surface of lever arm 48.

The volume of bag 50 may be about three liters so that if any fluid has collected in the peritoneal cavity, it also will be discharged along with the dialysis fluid. The counterweight is selected so that microswitch 54 is closed until a sufficient volume of fluid, preferably about 1500 grams, is collected in bag 50. At 1500 grams, the force of the counterweight is overcome and the lever arm 48 rotates about pin 46 to open microswitch 54. The microswitch is connected to an alarm signal in a manner which will be explained herein.

Normally, microswitch 54 is closed. However, if at a predetermined interval microswitch 54 is still closed, the alarm is activated to notify the patient that the expected quantity of fluid has not drained from the peritoneal cavity.

The means for receiving fluid discharged from the apparatus 22 may comprise any convenient receptacle such as a disposable bag. In the alternative it could be a conventional drain.

The container 14 is connected to both the means for heating and metering dialysis fluid 16 and the inlet of catheter 18. To this extent a length of tubing 60 is connected between the bottom opening 25 in container 14 and an arm of a "T" 62. Another length of tubing 64 is connected between the second arm of the "T" 62 and the opening 38 in the means for heating and metering dialysis fluid 16. The third arm of "T" 62 is connected by a length of tubing 66 to the catheter 18.

The outlet of the catheter 18 is connected to both the means for detecting discharge of fluid from the patient 20 and the means for receiving discharged fluid 22. To this extent a length of tubing 70 is connected between the catheter 18 and one arm of a "T" 72. Another length of tubing 74 is connected between a second arm of "T" 72 and the bag 50. The third arm of "T" 72 is connected to the means for receiving discharged fluid 22 by a length of tubing 76.

The lengths of tubing 60, 66, 70 and 76 pass through control means 24.

From FIG. 1 it is apparent that the control means 24 may comprise first and second valves 80 and 82. First valve 80 selectively opens and closes tubes 60 and 70. Second valve 82 selectively opens and closes tubes 66 and 76. The valves regulate the flow of fluid through the apparatus.

When valve 80 is open and valve 82 is closed, the fluid in container 14 is permitted to flow through tubes 60 and 64 into the heating and metering means 16. Simultaneously, fluid is drained from the patient through the catheter 18 and tubes 70 and 74 into bag 50.

When the valve 82 is open and valve 80 is closed, fluid flows from the heating and metering means through tubes 64 and 66 into catheter 18 and thence into the patient. Simultaneously fluid is drained from the bag 50 through conduits 74 and 76 into the discharge receiving means 22.

Thus, by controlling the duration of time for which the valves 80 and 82 are opened and closed and by regulating the volume of dialysis fluid which can be stored in the heating and metering means 16, an efficient, safe peritoneal dialysis apparatus is achieved. Significantly, it should be noted that bag 50 is provided on the downstream side of the patient in order to detect an insufficient drainage of fluid from the peritoneal cavity.

The control means 24 is illustrated in FIGS. 2–4. It comprises a housing 86 which rotatably supports a shaft 88 in bearings 89. The shaft 88 is connected by way of a clutch 90 to the output shaft 92 of a motor 94. Output shaft 92 is rotatably supported by bearing 95.

Shaft 88 supports cams 100 and 102 which operate valves 80 and 82 respectively, and cam 104 which operates microswitches 108 and 110. Cams 100 and 102 have profiles that correspond to FIG. 9 wherein it is seen that each valve 80, 82 opens slowly and closes quickly. The microswitches 108 and 110 are supported by housing 86 so that their operators can be displaced into a notch formed in the cam (see FIG. 8). Hence rotation of cam 104 through a complete revolution causes each microswitch to be tripped once. The cams 100 and 102 are supported on shaft 88 so that they are 180° out of phase with respect to each other. Thus when one of valves 80 and 82 is open, the other is closed. As will be explained in greater detail herein, the power to motor 94 is supplied through microswitches 108 and 110. When the switch operators fall into the notch in the cam, the motor 94 is stopped. This positions the valves 80 and 82 in accordance with the configuration of cams 100 and 102 until the motor is energized through the microswitch whose operator is not in the notch.

Each valve includes a stem 114 with a cross bar 118 at one end and, if desired, a roller 120 at its other end. Each valve stem 114 includes a radially directed flange 122 near roller 120.

The valve stems 114 are supported in apertures 123 formed in a support member 124 mounted in housing 86. Each of valve stems is biased toward its respective cam 100, 102 by a spring 126 which bears against the flange 122.

A plate 130 is supported in spaced relation from the front wall of housing 86 by a suitable hinge 132. Suitable latching means such as member 134 may be provided for retaining plate 130 in the position illustrated in FIG. 2.

Plate 130 supports a housing 138 having the appearance of a frame with a central opening 139. The housing 138 is comprised of two separate members 140, 142 which have grooves in which the tubes can be received. When the members 140, 142 are assembled the tubes are held in the position illustrated in FIGS. 2 and 4. Thus, tubes 60 and 70 are positioned so that they can be pinched closed by valve 80. Tubes 66 and 76 are positioned so that they can be pinched closed by valve 82.

A layer of relatively soft backing material 148 such as foam rubber, felt or the like is secured to plate 130 adjacent tubes 60, 70, 66 and 76.

Suitable means is provided for selectively energizing motor 94 at predetermined intervals during the dialysis treatment. The motor causes shaft 88 to rotate with the result that the tubes 60 and 70, and 66 and 76 are alternately pinched and released to permit fluid to flow through the apparatus.

Figure 8:
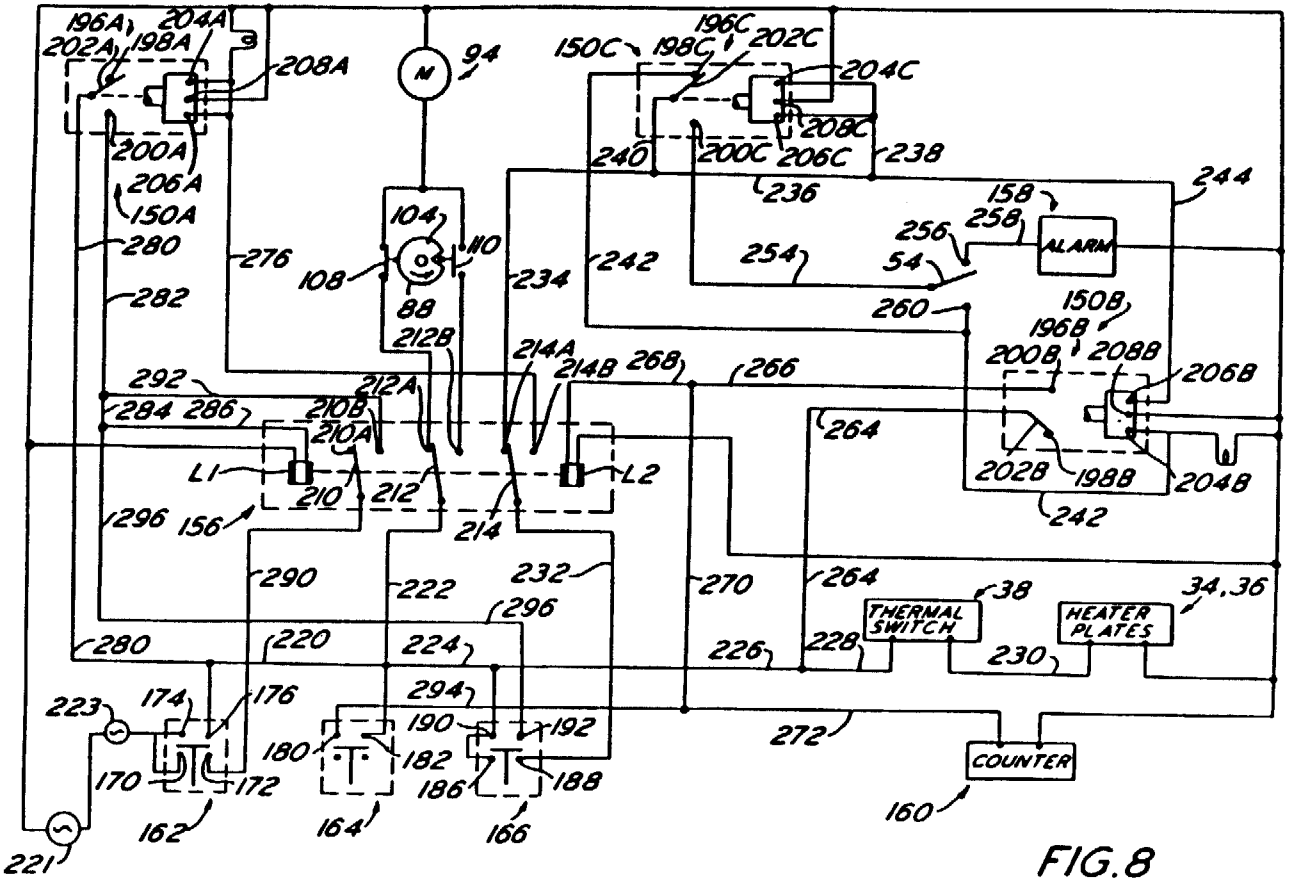
FIG. 8 is a schematic view of the circuitry for operating the apparatus.

The energization means for the motor comprises the circuit illustrated schematically in FIG. 8.

The circuit comprises timers 150A, 150B and 150C, a two-position latching relay 156, an alarm signal 158 and a counter 160.

Additionally, the circuit includes the heating plates 34 and 36, thermal switch 38, switch 54, motor 94 and switches 108 and 110.

The circuit is energized by closing on-off switch 162. Switch 164, which may be called the fill switch, is operative when closed to cause the dialysis fluid in bag 35 to enter the patient by way of catheter 18. Switch 166, which may be called the drain switch, is operative when closed to cause the dialysis fluid in the patient to be discharged therefrom into bag 50.

On-off switch 162 may be a two-position push button switch. When the switch is "OFF" a circuit is completed across terminals 170 and 172. When the switch is "ON" a circuit is completed across terminals 174 and 176. Fill switch 164 may be a push button switch which is biased to a normally "OPEN" position. However, when the push button is monentarily "CLOSED," a circuit is enabled across terminals 180 and 182.

Drain switch 166 may be a push button switch of the same type as switch 164 in that it is biased to a normally "OPEN" position. In its "OPEN" position it enables a circuit across terminals 186 and 188. When this switch is momentarily "CLOSED" a circuit is enabled across terminals 190 and 192.

Timers which may be used satisfactorily in the invention are identified commercially as Singer Industrial Timers, Type GTD, 30 minutes. These timers may be set to run for a maximum time of 30 minutes. Each timer 150A, 150B and 150C is essentially the same. Thus, the same part in each timer is identified by the same reference numeral with the different timers being distinguished by the letters "A," "B" and "C" following the numerals.

The following description will suffice for all timers 150. Each timer includes a switch 196 which is comprised of contacts 198 and 200 and throw 202. It also includes a timer motor which is connected by an electrically energized clutch to throw 202.

The timer motor runs continuously as long as power is applied to motor terminal 204.

The clutch is energized as long as power is applied to clutch terminal 206. Every time the clutch is energized, the timer is reset to the maximum time thereon (this feature is an aspect of the particular timer identified herein).

Both the timer motor and the clutch are connected to common terminal 208. While the motors are connected to the throws by the clutches, the throws 202 engage contacts 198 in each switch 196. When each timer has run out, the throws 202 move from contacts 198 to contacts 200.

Relay 156 includes three separate but interconnected single throw switches. In each switch the throw, 210 212 and 214, respectively is movable between first and second contacts 210A and 210B, 212A and 212B and 214A and 214B.

The throws are shifted by energizing coil "L1" or "L2". Energization of coil "L1" completes a circuit through contacts 210A, 212A and 214A. Energization of coil "L2" completes a circuit through contacts 210B, 212B and 214B. The throws remain in engagement with the contacts until the other coil ("L1" or "L2") is energized, then they shift.

The source of electromotive force 221, which may be an ordinary electrical outlet, is connected by way of fuse 223 to terminals 170 and 174 on on-off switch 162.

The circuit is designed so that when the apparatus is shut off the relay throws are at rest on contacts 210A, 212A and 214A. Therefore the apparatus always starts on that portion of its cycle which permits fluid to be drained from the patient into bag 50. The mechanism by which this occurs is explained herein.

Upon the closing of on-off switch 162 on terminals 174 and 176 a number of circuits are completed or enabled from the source of power 221 and fuse 223. These circuits permit fluid to be discharged from the patient for a predetermined interval as will be explained herein.

Thus, a circuit is completed to motor 94 from on-off switch terminal 176 by way of lines 220, 222 and through switch 108. A circuit is completed to thermal switch 38 and heater plates 34, 36 by way of lines 220, 224, 226, 228 and 230.

The motors and clutches on timers 150B and 150C are energized and the timers begin to wind down by virtue of circuit through drain switch 166 and relay 156. The circuit includes lines 224, terminals 190, 186 and 188, line 232, relay contact 214A and line 234.

The motor and clutch of timer 150C is energized by way of line 234 and lines 236 and 238 which are connected to timer motor terminal 204C and clutch terminal 206C.

Switch 196C receives power by way of lines 234, 240 and throw 202C. Since throw 202C is touching contact 198C, a circuit is completed by way of line 242 to the motor terminal 204B in timer 150B. An indicator lamp may be connected to line 242 to indicate when the timer motor is energized. Clutch terminal 206B receives power from line 236 by way of line 244.

The motor 94 causes shaft 88 to rotate in the direction indicated by the arrow in FIG. 8 until the operator of switch 108 falls into the notch in cam 104. This opens the circuit to the motor thereby halting the rotation shaft 88. By virtue of the positions of cams 100 and 102 on shaft 88 they have been rotated to the position illustrated in FIG. 2 where valve 80 is open and valve 82 is closed. As illustrated in FIG. 1, when the valves are in this configuration dialysis fluid is permitted to drain from container 14 to the heating and metering means 16 and at the same time fluid is permitted to drain from the patient by way of catheter 18 into the bag 50.

If for some reason, cam 104 is not in the position illustrated when on-off switch 162 is closed and switch 108 is open, the motor 94 will not operate since the valves 80 and 82 will be in the correct positions to permit fluid to be drained from the patient.

Timer 150C is set to run for a shorter time than timer 150B. Timer 150C cooperates with switch 54 to indicate that fluid is draining from the patient at an adequate rate. To this extent a circuit is normally enabled through switch 54 by way of contact 200C in timer 150C, line 254, switch contact 256 and line 258 to alarm 158. But when the weight of fluid in bag 50 reaches 1500 grams, or any predetermined weight deemed desirable, the throw in switch 54 is moved to contact 260.

With the foregoing in mind, when timer 150C runs out, as for example fifteen minutes after it is energized, throw 202C moves to contact 200C. If the predetermined quantity of fluid is not in bag 50, the circuit through alarm 158 is completed by way of line 254, contact 256 and line 258. The alarm 158 may be visible, audible or a combination of both, provided it alerts the patient to the fact that inadequate drainage from the body is taking place. Since there is no power in line 242, the motor in timer 150B is stopped. Thus, the apparatus remains in the drain portion of the cycle and the alarm 158 remains energized until the apparatus is shut off or the fill switch 164 is depressed.

In an adequate amount of fluid is in bag 50 when timer 150C runs out, the alarm is bypassed and power to motor terminal 204B is achieved by way of line 254, contact 260 and line 242.

Assuming that there has been adequate drainage to bag 50, when the time on timer 150B runs out, throw 202B moves to contact 200B to start filling the patient with dialysis fluid. This energizes coil "L-2" in relay 156 by way of lines 226, 264, throw 202B, contact 200B, lines 266 and 268. Coil "L2" moves all of the throws in the relay clockwise so that circuits are completed to terminals 210B, 212B and 214B.

Energization of coil "L2" energizes counter 160 by way of lines 266, 270 and 272. Hence a count is taken on each time the circuit shifts to cause dialysis fluid to enter the patient.

Clockwise movement of the relay throws 210, 212 and 214 completes or enables a number of circuits.

A circuit is completed to motor 94 through line 222, relay contact 212B and through switch 110. The switch is closed since the notch in cam 104 is now adjacent switch 108. The motor rotates shaft 88 until the operator on switch 110 falls into the notch whereupon the motor stops rotating the shaft. At this point valves 80 and 82 are in the positions illustrated in FIG. 1 wherein fluid is permitted to fill the patient by way of catheter 18 from the heating and metering means 16 and the fluid in bag 50 is permitted to be discharged to the drain means 22.

The motor and clutch on timer 150A are energized and the timer begins to wind down by way of a circuit through relay throw 214, relay contact 214B and line 276. Line 276 is connected to motor terminal 204A and clutch terminal 206A. An indicator lamp may be coupled to motor terminal 204 to indicate that the motor is energized.

The throw 202A in switch 196A is on contact 198A while the timer is running. When the time on timer 150A runs out, after, for example 30 minutes, throw 202A shifts to contact 200A to complete a circuit through coil "$L_1$" by way of line 280, relay throw 202A and lines 282, 284 and 286.

Energization of coil "$L_1$" shifts all the relay throws in relay 156 counterclockwise so that they engage contacts 210A, 212A and 214A. This completes a circuit through timer 150B and timer 150C so that the cycle is repeated as described above. In the event that timer 150C should run out before an adequate amount of fluid is received in bag 50, alarm 158 will be energized.

When timer 150B runs out the relay 156 shifts and the motor 94 energized to rotate shaft 88 to permit dialysis fluid to again fill the patient. At the same time, timer 150A is energized.

Significantly, it should be noted that the timers are reset to the maximum time thereon each time they are energized. In timers 150A and 150B the maximum time is externally adjustable. To this extent, they may be mounted on a panel and have knobs extending therefrom for that purpose.

On the other hand, timer 150C is designed to be non-adjustable. Thus, it may be set at the factory. It is preferably permanently mounted within an enclosing structure so that it cannot be tampered with by the user.

At any time in its cycle the apparatus may be shut down by moving switch 162 to the "OFF" position so that it completes a circuit across terminals 170 and 172.

If the relay throws are in their clockwise positions when on-off switch 162 is moved to its "OFF" position, a circuit is completed to coil "L1" from terminals 170 and 172 by way of line 290, relay contact 210B, and lines 292, 284 and 286. This moves the throws counterclockwise which then opens the circuit from on-off switch 162 since relay contact 210A is not connected to the rest of the circuit.

If, on the other hand, the relay is closed on contact 210A, moving switch 162 to its "OFF" position so that it completes a circuit across terminals 170 and 172 merely shuts down the apparatus.

The apparatus can be switched from the drain cycle to the fill cycle or from the fill cycle to the drain cycle by depressing fill switch 164 or drain switch 166 respectively.

For example, if the apparatus is draining fluid from the patient and it is desired to switch it to fill the patient, switch 164 is depressed momentarily to complete a circuit across terminals 180 and 182. This completes a circuit from the source of electromotive force through contacts 174 and 176, line 220, through switch 164 by way of terminals 180 and 182, and line 294. Counter 160 is energized by way of lines 294 and 272. Coil "L2" is energized by way of lines 294, 270, and 268. When coil L2 is energized, it shifts the throws (they are in their counterclockwise position when fluid is draining from the patient). This completes a circuit to relay contact 212B and a circuit to relay contact 214B so that circuits are completed through switch 110 to motor 94 and to timer motor and clutch terminals 206A and 204A in timer 150A. Shaft 86 rotates until switch 110 opens thereby deenergizing motor 94. This opens valve 82 to fill the patient from the metering and heating means 22.

When the time on timer 150A runs out, throw 202A moves to contact 200A. This completes a circuit from terminal 176 in on-off switch 162 to coil "L1" by way of line 280, throw 202A, contact 200A and lines 282, 284 and 286. Energization of coil "L1" shifts the relay throws counterclockwise to energize and reset timers 150B and 150C and motor 94 (through switch 108) to start the drain portion of the cycle.

The drain cycle continues as explained above with both timers 150C and 150B being energized. If timer 150C runs out before an adequate amount of fluid is in bag 50 an alarm is sounded.

On the other hand, if an adequate amount of fluid is in bag 50 when timer 150B runs out, the relays are again thrown and the fill portion of the cycle takes over.

If the apparatus is in the fill portion of its cycle and it is desired to shift it to the drain portion, switch 166 is depressed momentarily to complete a circuit across terminals 190 and 192. This completes a circuit to coil "L1" by way of terminal 192 and lines 296 and 286. Energization of coil "L1" shifts the relay throws counterclockwise to complete circuits to relay contacts 212A and 214A so that circuits are completed to motor 94 and to timers 150B and 150C. In this regard, the circuit components assume the same configuration that they have when on-off switch 162 is moved to its "ON" position as described in detail above.

From the foregoing it is apparent that at any part of its cycle the apparatus can be shifted to the opposite part of the cycle.

In order to use the apparatus described, each of the components of the system, namely, container 14, metering and heating means 16, the patient and catheter 18, the weighing means 20 and the drain 22 are arranged so that each component has a higher elevation than the component following it so that the natural tendency of the dialysis fluid in container 14 is to flow through the apparatus.

Figure 9:
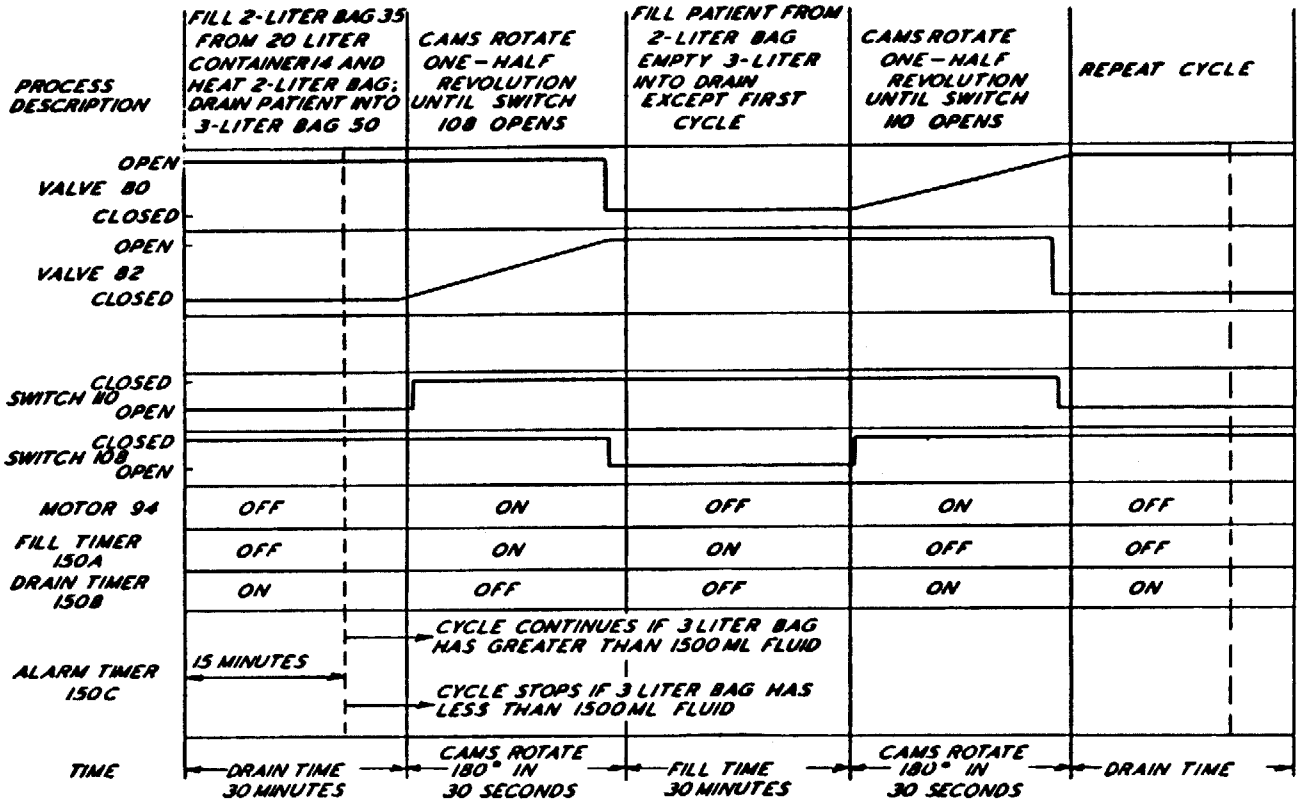
FIG. 9 is a drawing graphically portraying the operation of the apparatus.

The sequence of operation of the apparatus is shown in FIG. 9. The apparatus can go through a complete cycle in up to one hour. Up to 30 minutes can be used to fill the patient and up to 30 minutes can be used to drain the patient. The duration of the fill and drain intervals are controlled by timers 150A and 150B. Since the timers are externally adjustable these periods can be varied as desired.

The motor 94 is energized at the end of each fill and each drain interval. The motor is selected so that each time it is energized shaft 88 rotates through half a turn in about 30 seconds. As explained earlier the motor is energized at the end of each fill and drain interval. Cams 100 and 102 are profiled to enable valves 80 and 82 to gradually open over each thirty second interval of shaft rotation, but to close abruptly. This is so that the dialysis fluid does not surge or drip through the tubing. During each thirty second period of cam rotation, the positions of valves 80 and 82 are reversed, and, due to cam 104, one of microswitches 108, 110 is opened while the other is closed.

A commercial embodiment of the invention would comprise sufficient dialysis fluid in container 14 to discharge a two liter does of dialysis fluid into the patient every half hour with the succeeding half hour being consumed in withdrawing the dialysis fluid. Thus, the heater bag acts as a measuring device in order to control the amount of fluid being introduced to the peritoneal cavity in any given time.

It is contemplated that with the present apparatus a complete dialysis can be achieved in a period of about 10 hours as opposed to an interval of 36 to 72 hours as in present procedures.

The substantial reduction in time is achieved by virtue of the fact that the dialysis fluid is changed rather rapidly.

Thus, it is a well known fact that in an osmotic process, as the fluids on each side of the membrane approach equilibrium, the rate of exchange across the membrane decreases. Thus, it is advantageous to change the dialysis fluid as the rate of transfer across the peritoneal membrane begins to slacken.

This can readily be done with the present apparatus by merely externally adjusting the time available on timers 150A and 150B.

At the same time since the presence of an attendant is not necessary in order to change the fluid in container 14, a sufficient amount of fluid in order to perform the entire dialysis may be made available at one time. It is contemplated that an adequate amount of fluid to satisfactorily dialyze an adult patient would be about 20 liters. Thus, over a period of 10 hours, at a rate of 2 liters per cycle, the entire quantity of fluid would be consumed.

Significantly, at the end of each cycle of the apparatus, the fluid discharged from the peritoneal cavity is weighed in order to assure that the patient is draining properly. In the event that inadequate drainage is taking place, a suitable alarm is activated.

A further safety device is present by virtue of the fact that when the apparatus is initially turned on as, by pushing switch 162 to close a circuit across terminals 174 and 176 the apparatus automatically starts on a drain cycle. Thus, there is no possibility that two liters of dialysis fluid would be in the patient as two additional liters are being introduced.

Finally, it should be noted that the apparatus always shuts off in the drain position.

While the invention has been described with respect to one preferred embodiment thereof, it is apparent that many other forms and embodiments will be obvious to those skilled in the art in view of the foregoing description. Thus, the scope of the invention described herein should not be limited by that description but, rather, only by the scope of the claims appended hereto.

We claim:

1. A dialysis apparatus comprising first means for supplying dialysis fluid, second means for measuring a predetermined quantity of dialysis fluid, a catheter, third means for detecting a minimum quantity of dialysis fluid, means for supporting said first means above said second means, said second means above said catheter, and said third means below said catheter so that dialysis fluid moves through said apparatus under the force of gravity, fluid flow conduits interconnected between said first and second means[,] *and between* said second means and said catheter and *between* said catheter [in] *and* said third means, fourth means *including a single actuator for plural valves* for *simultaneously* regulating the flow of dialysis fluid [and] *in* said [conduits] *conduit* between said first and second means and *the conduit between* said catheter and said third means *in a manner so that flow is simultaneously on or off*, fifth means *including a single actuator for plural valves* for *simultaneously* regulating the flow of dialysis fluid *in the conduit* between said second means and said catheter[,] and *a conduit* from said third means *in a manner so that flow is simultaneously on or off*, and means for controlling said *actuators for said* fourth and fifth means to alternately permit flow of dialysis fluid in the conduits regulated thereby so that the dialysis fluid is permitted to flow through said apparatus and a patient and then from said third means.

2. A dialysis apparatus as defined in claim 1 including an alarm, means coupling said third means to said alarm, and means for enabling said alarm if said third means fails to detect a minimum quantity of dialysis fluid.

3. A dialysis apparatus as defined in claim 2 wherein said third means comprises a frame, an arm, said arm being pivotally supported by said frame intermediate its ends, a fluid receptacle coupled to said arm on one side of said pivot, means comprising a counterweight coupled to said arm on the other side of said pivot, and said means for enabling said alarm is disposed adjacent said arm for actuation thereby if the weight of dialysis fluid in said fluid receptacle is insufficient to overcome the force of said counterweight means.

4. A dialysis apparatus as defined in claim 1 wherein said second means [includes] *is removably mounted in a housing* means for heating dialysis liquid [therein] *in said second means* to a predetermined temperature.

5. A dialysis apparatus as defined in claim 1 including a fluid flow conduit extending from said third means, and a discharge receptacle connected to said last named fluid flow conduit to receive dialysis fluid from said third means.

6. A dialysis apparatus as defined in claim 1 wherein said control means comprises a shaft, first and second cams mounted on said shaft, one of said cams controlling said fourth means *actuator*, the other cam controlling said fifth means *actuator*, energizable means for rotating said shaft, and means for selectively energizing and de-energizing said energizable means to selectively rotate said shaft.

7. A dialysis apparatus comprising first means for supplying dialysis fluid, second means for measuring a predetermined quantity of dialysis fluid, a catheter, third means for detecting a minimum quantity of dialysis fluid, said third means comprises a frame, an arm, said arm being pivotedly supported by said frame intermediate its ends, a *removable* fluid receptacle coupled to said arm on one side of said pivot, means comprising a counter weight coupled to said arm on the other side of said pivot, and said means for enabling said alarm is disposed adjacent said alarm for actuation thereby if the weight of dialysis fluid on said fluid receptacle is insufficient to overcome the force of said counter weight means, fluid flow conduits interconnected between said first and second means, said second means and said catheter, and said catheter and said third means, fourth means for *simultaneously* regulating the flow of dialysis fluid in said conduits between said first and second means and said catheter [in] *and* said third means, fifth means for *simultaneously* regulating the flow of dialysis fluid between said second means and said catheter, and from said third means, and means for controlling said fourth and fifth means to alternately permit flow of dialysis fluid in the conduits regulated thereby so that the dialysis fluid is permitted to flow through said apparatus and the patient and then from said third means, said control means comprises a shaft, first and second cams mounted on said shaft, one of said cams controlling said fourth means, and other cam controlling said fifth means, energizable means for rotating said shaft, and means for selectively energizing and de-energizing said energizable means to selectively rotate said shaft.

8. A dialysis apparatus comprising first and second means for regulating the flow of dialysis fluid through said apparatus, means coupling said first and second regulating means to each other so that when said coupling means is a first position said first regulating means stops the flow of dialysis fluid and said second regulating means permits the flow of dialysis fluid, and when said coupling means is in a second position said first regulating means permits the flow of dialysis fluid while said second regulating means stops the flow of dialysis fluid, selectively energizable means for alternatively positioning said coupling means between its first and second positions, said selectively energizable means being mechanically connected to said coupling means, first, second and third timers, said first timer for controlling the duration of time in which said coupling means is in a first position, said first timer including means to emit a control signal when said first timer times out, electrical means for transmitting said control signal from said first timer to said selectively energizable means, said selectively energizable means adapted to be energized in response to said control signal so that said selectively energizable means causes said coupling means to be positioned in the second position, said electrical means also to transmit said control signal to said second and third timers, said second and third timers to automatically reset and start timing out in response to such signal, said third timer for controlling the duration of time in which said coupled regulating means are in the second position, said third timer including means to emit a control signal when said third timer times out, electrical means for transmitting said control signal from said third timer to said selectively energizable means, said selectively energizable means adapted to be energized in response to said control signal so that said selectively energizable means causes said coupling means to be positioned in the first position, said electrical means also to transmit said control signal to said first timer, said first timer to automatically reset and start timing out in response to such signal, an energizable alarm and a switch, said switch being operative to enable said alarm upon a condition, said second timer having a shorter timing duration than said third timer and being electrically connected to said third timer and said energizable alarm so that if the alarm is enabled when said second timer times out, said alarm is energized and said third timer stops timing out until said condition no longer exists.

9. A dialysis apparatus defined in claim 8, including overriding means for selectively generating a control signal to said first timer in said selectively energizable means, said first timer to automatically rewind and start timing out in response to said control signal, said selectively energizable means to be energized in response to said control signal so that selectively energizable means causes said coupling means to be positioned in the first position, said overriding means to be operable independently of said first, second or third timers.

10. A dialysis apparatus defined in claim 8, including overriding means for selectively generating a control signal to said second and third timers and to said selectively energizable means, said second and third timers to automatically rewind and start timing out in response to said control signal, said selectively energizable means to be energized in response to said control signal so that selectively energizable means causes said coupling means to be positioned in the second position, said overriding means to be operable independently of said first, second or third timers.

*11. A prepackaged sterilized peritoneal dialysis apparatus comprising:*

*(a) a first collapsible measuring bag adapted to receive dialysis fluid and having a single inlet-outlet,*

*(b) a second collapsible weighing bag adapted to receive dialysis fluid from a patient and having a single inlet-outlet,*

*(c) at least six lengths of flexible tubing,*

*(d) a first length of said tubing having one end directly connected to the inlet-outlet of said first bag, a second length of said tubing having one end connected at a junction to the other end of said first length of tubing, the other end of said second length of tubing being adapted to be connected to a source of dialysis fluid,*

*(e) a third length of said tubing having one end adapted to be in communication with a catheter, the other end of said third length of tubing being connected through a junction to the interconnected ends of said first and second lengths of tubing,*

*(f) a fourth length of said tubing having one end directly connected to the inlet-outlet of said second bag,*

*(g) a fifth length of said tubing having one end in communication with said third tubing, the other end of said fifth length of tubing being connected through a junction to the other end of said fourth length of tubing,*

*(h) a sixth length of tubing having one end adapted to be connected to a waste disposal, the other end of said sixth length of tubing being connected at the last mentioned junction to the interconnected ends of said fourth and fifth lengths of tubing,*

*(i) whereby said third length of tubing may be used to feed fluid to a patient and the fifth tubing may be used to transfer fluid drained from a patient to said second bag via said fourth tubing.*

* * * * *